(12) United States Patent
Van der Loos et al.

(10) Patent No.: US 6,468,234 B1
(45) Date of Patent: Oct. 22, 2002

(54) SLEEPSMART

(75) Inventors: H. F. Machiel Van der Loos, Woodside, CA (US); Joel S. Ford, Mountain View, CA (US); Hisato Kobayashi, Tokyo (JP); Joseph Norman, Menlo Park, CA (US); Tomoaki Osada, Fujisawa (JP)

(73) Assignees: The Board of Trustees of the Leland Stanford Junior University, Stanford, CA (US); The United States of America as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 09/710,495

(22) Filed: Nov. 10, 2000

Related U.S. Application Data

(60) Provisional application No. 60/218,238, filed on Jul. 14, 2000.

(51) Int. Cl.[7] .................................................. A61B 5/00
(52) U.S. Cl. ........................ 600/595; 600/549; 128/920; 340/573.1
(58) Field of Search ................................. 600/300–301, 600/544–545, 549, 590, 587; 128/903, 904, 920–925; 705/2, 3; 340/573

(56) References Cited

U.S. PATENT DOCUMENTS

| | | |
|---|---|---|
| 4,320,766 A | 3/1982 | Alihanka et al. |
| 5,038,137 A | 8/1991 | Lloyd |
| 5,435,317 A | 7/1995 | McMahon et al. |
| 5,611,096 A | 3/1997 | Bartlett et al. |
| 5,684,460 A | 11/1997 | Scanlon |
| 5,796,340 A | 8/1998 | Miller |
| 5,844,488 A | 12/1998 | Musick |
| 5,846,206 A * | 12/1998 | Bader ......................... 600/534 |
| 5,882,300 A | 3/1999 | Malinouskas et al. |
| 5,902,250 A | 5/1999 | Verrier et al. |
| 5,914,660 A | 6/1999 | Mesibov et al. |
| 5,957,854 A | 9/1999 | Besson et al. |
| 5,989,193 A | 11/1999 | Sullivan |
| 5,999,846 A | 12/1999 | Pardey et al. |
| 6,011,477 A * | 1/2000 | Teodorescu et al. ..... 340/573.1 |
| 6,080,106 A * | 6/2000 | Lloyd et al. ................ 600/300 |
| 6,126,595 A * | 10/2000 | Amano et al. .............. 600/300 |
| 6,269,339 B1 * | 7/2001 | Silver ........................... 705/2 |

* cited by examiner

*Primary Examiner*—Kevin Shaver
*Assistant Examiner*—Michael C Astorino
(74) *Attorney, Agent, or Firm*—Lumen Intellectual Property Services, Inc.

(57) ABSTRACT

A method and apparatus for measuring sleep quality that utilizes sensors incorporated in a sheet which is laid on top of a conventional mattress on which the subject sleeps. The sensors can collect information such as the subject's position, temperature, sound/vibration/movement, and optionally other physical properties. The apparatus for monitoring an individual's sleep quality is comprised of one or more layers of arrays of integrated sensors, which can be incorporated in layer pads, which is then placed on a conventional mattress; one or more controllers coupled with the arrays of integrated sensors in each layer pad for the purpose of acquiring data from the sensors; a real-time analysis software for analyzing data acquired by the controller from the array of integrated sensors; an interface software for collecting user lifestyle data; a lifestyle correlation software for correlating the lifestyle data with the data acquired by said array of sensors; one or more active components to improve sleep quality based on the data acquired through the sensors and the lifestyle data. The array of sensors provide one or more of the following data: position, temperature, sound, vibration, and movement data. Each layer pad can be individually removed or added as necessary depending on the data being collected.

28 Claims, 2 Drawing Sheets

SLEEPSMART

CROSS-REFERENCE TO RELATED APPLICATIONS

Provisional U.S. application No. 60/218,238 filed Jul. 14, 2000, under the title "SensorBed" by Steven Woodward, which is hereby incorporated by reference in full. At the time the present invention was made it was obligated to be assigned to the same entity as the invention of the referenced provisional U.S. application No. 60/218,238.

BACKGROUND OF THE INVENTION

1. Field of the Invention

The present invention relates to sleep monitoring and particularly to a method and apparatus for monitoring a person's sleep through the use of integrated sensors in layer pads.

2. Description of the Related Art

Inadequate sleep is a chronic problem for a significant portion of the population. Consequently, everyday activities, level of function and safety are negatively impacted. The quality of sleep has a direct effect upon waking performance, attitude, and quality of life.

Traditional sleep monitoring or polysomnography is performed in a sleep laboratory, using ten to twenty body-surface sensors (electrodes, elastic bands, etc.) to record the electroencephalogram, electro-oculogram, electromyogram, electrocardiogram, respiratory movement/efforts at thorax and abdomen, oral/nasal airflow, and blood oxygen saturation. The attachment of sensors using glue and tapes and the routing of wires against the skin typically requires ninety minutes or more and is performed by a trained polysomnographic technician. Ambulatory versions of polysomnography uses portable recorders so that the sleep monitoring can occur at the home of the patient. However, a polysomnographic technician is still needed and the same amount of time and effort is necessary to connect all the sensors to the body. All this activity leading up to the patient actually going to sleep dramatically alters a night of "natural sleep".

Several previous attempts have been made on incorporating sensors into a sleeping mattress so as to do away with the need to connect sensors to the patient's body for the purpose of gathering data. However, most of these applications only utilize one sensor for collecting one type of data and are therefore not very useful when compared to traditional polysomnography.

OBJECTIVES AND ADVANTAGES

A principal objective of the present invention is to provide a home-use sleeping monitoring system that does not require wired sensors to be attached to a subject's body. The present invention utilizes sensors incorporated in a layer pad that is laid over a conventional mattress, wherein the sensors can collect medically-significant data from the subject. The signals from the sensors are collected by a data acquisition unit and converted to data that can be analyzed or stored for later analysis. This system does not require any specialized training to use as there are no sensors to attach to the body. This system requires no extra effort on the subject's part to prepare for the sleep data collection prior to sleeping. Because of all these advantages, this system can be used in the subject's home for an extended period of time to collect continuous sleep data.

The present invention can also be used for monitoring infants diagnosed with a high risk of Sudden Infant Death Syndrome (SIDS) and for field emergency applications.

SUMMARY OF INVENTION

In view of the forgoing objectives, a method of the present invention utilizes sensors incorporated in a layer pad which is laid on top of a conventional mattress on which the subject sleeps. The sensors can collect information such as the subject's position, temperature, sound, vibration, movement, and optionally other physical properties.

The apparatus for monitoring an individual's sleep quality comprises one or more layers of arrays of integrated sensors, which can be incorporated in layer pads, which is then placed on a conventional mattress; one or more controllers coupled with the arrays of integrated sensors in each layer pad for the purpose of acquiring data from the sensors; a real-time analysis software for analyzing data acquired by the controller from the array of integrated sensors; an interface software for collecting user lifestyle data; a lifestyle correlation software for correlating the lifestyle data with the data acquired by said array of sensors; one or more active components to improve sleep quality based on the data acquired through the sensors and the lifestyle data. The array of sensors provide one or more of the following data: position, temperature, sound, vibration, and movement data. Each layer pad can be individually removed or added as necessary depending on the data being collected.

The controller can be an embedded controller, a desktop personal computer or a laptop computer.

The real-time analysis software transforms the data collected by the controller from time domain to event and/or frequency domain. The real-time analysis software can also extract body temperature, position and movement, mattress pressure, breathing and heart rate, snoring, and bruxism information.

The real-time analysis software can compute means, variances, characteristic frequencies, and counts from the data and calculate an index of nightly restlessness.

The user lifestyle data collected can be such things as the last time and how much a meal was eaten, how much medication, vitamins, and products containing caffeine and alcohol were consumed, estimate of stress level, amount and intensity of exercise, and an estimation of the quality of sleep just experienced overnight.

The lifestyle correlation software provides correlation analysis between any of the data collected by the controller and by the lifestyle software. The lifestyle correlation software utilizes aggregate data from several days to several months to compute and present long-term averages, trends, and singularities.

The active components that alter the quality of sleep can be one or more of the following: a temperature control system to alter the mattress or room temperature based on the body temperature data, a wake-up alarm that is activated based on a particular point in a person's circadian rhythm, a lighting control system to change the ambient light level using window blinds or computer-controlled room lights, and an active tilting mattress support activated to encourage a person to roll over to alleviate snoring.

BRIEF DESCRIPTION OF THE DRAWINGS

The foregoing and other objects, features and advantages of the present invention will be apparent from the following detailed description of the preferred embodiments of the invention, reference being made to the accompanying drawing, in which like reference numerals indicate like parts and in which.

DETAILED DESCRIPTION OF THE EMBODIMENTS

Although the following detailed description contains many specifics for the purposes of illustration, anyone of ordinary skill in the art will appreciate that many variations and alterations to the following details are within the scope of the invention. Accordingly, the following preferred embodiment of the invention is set forth without any loss of generality to, and without imposing limitations upon, the claimed invention.

Figure 1:
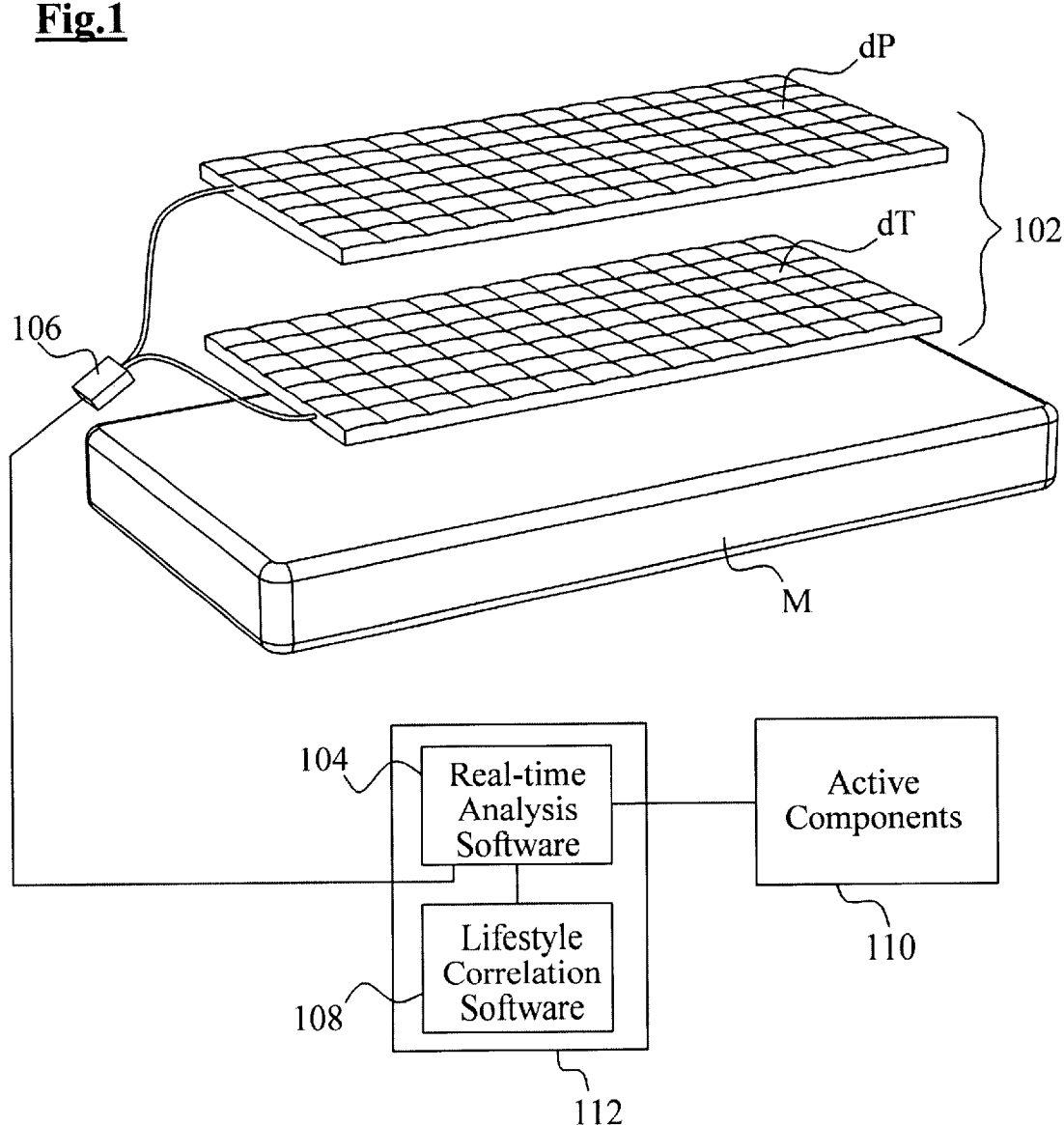
FIG. 1 is a diagram illustrating an embodiment of the present invention.

FIG. 1 illustrates the system of the present invention, which has five main subsystems that are essential to the overall purpose of the invention. They are 1) the layer pads 102 and controller 112, 2) the real-time analysis software 104, 3) the interface software 106, 4) the lifestyle correlation software 108, and 5) the active components to improve sleep quality 110. These subsystems can be used in any combination, and subsystems can be added or subtracted as functional needs dictate.

1. Layer pad 102 and controller 112. A layer pad 102 is used to hold an array of integrated sensors and this layer pad 102 can be placed over a conventional mattress such as a foam mattress. The integrated sensors can provide data for measuring position, temperature, sound, vibration, movement, and optionally other physical properties through additional sensors. Each layer pad 102 can have sensors that provide one or more of the above data. Layer pads 102 with these sensors can be added or removed as necessary depending on the type of data being collected. In the example of FIG. 1, the layer pads 102 are a temperature sensor pad dT and a pressure sensor pad dP illustrated above a commercial mattress M. For the purpose of visibility the layer pads 102 are shown in FIG. 1 above their operational position, which is directly on top of the commercial mattress M. This modular design also allows for easier repair of the sensors as each layer pad 102 can be replaced individually. It is clear to one skilled in the art that the temperature sensor pat dT and the pressure sensor pad dP may be physically combined in a single pad. This single pad may include other sensors for recognizing sleep behaviors as is known to those skilled in the art.

The array of sensors also allows the selection and analysis of zones of sensors in the areas of interest such as the abdomen area. Each sensor array has a low spatial resolution: approximately 10 cm between each sensor. In addition to lower cost due to the low number of sensors, it is also possible to modify the data collection rate from certain sensors that are providing high-quality data. There are no wires attached to the body, and the person will not be aware of the presence of the layer pad(s) or other sensors. Other sensors may include those worn on the body, such as in watch bands, finger rings, or adhesive sensors, but telemetry, not wires, would be used to communicate with the controller. This is a major advantage over tradition monitoring systems where a subject has to wear numerous wired sensors on their bodies which is both uncomfortable and alters the social context of the process of going to sleep. The controller 112 for the system of the present invention can be a desktop PC, a laptop computer, an embedded controller, or a handheld device (such as a handheld computer or a personal digital assistant) with two requirements: it must have data acquisition capability and have the ability to stay on all night.

2. Real-time analysis software 104. The real-time analysis software 104, based predominantly on the theory of wavelet transformations, transforms the data from the sensors from the time domain to the event and/or frequency domain. For instance, with respect to a heart beat detection, a wavelet transformations (WT) algorithm is applied individually to the most recent 5 seconds of each of the data streams from each force sensor. The amplitudes of the WT output signals are then compared, and the sensor with the highest is selected. This typically correlates with the sensor that happens to be closest to the heart at that time. The heart beat frequency is then easily measured by using a Fourier transform on the output of the WT algorithm, since the WT significantly cleans up the really noisy signal and makes the Fourier transform work much better. Then one can pick up the location of the main peak in the frequency domain and that is the heart rate. The software extracts information such as body temperature, position and movement, mattress pressure, breathing and heart rate, as well as episodes of snoring and teeth grinding (bruxism). With additional sensors, information such as bedroom temperature, ambient light, brain wave changes, and blood oxygen content can also be measured. For a long period of sleep, the real-time analysis software 104 will extract mean and variance of cyclic data such as heart rate and breathing rate, and can extract episodes that have characteristic frequencies, such as snoring and bruxism. The real-time analysis software 104 can also extract a count (e.g. the number of episodes) of body shift episodes during the night, and from that calculate an index of nightly restlessness (e.g. in units of events-per-hours). The real-time analysis software 104 can also apply sensor fusion techniques in the detection of events or characteristic frequencies to reduce event detection errors in the case of confounding information. For example, an abnormally low body pressure in all sensors could indicate a massive sensor failure or simply that the person got out of bed in the middle of the night. A correlation with a slowly reducing temperature reading (bed cooling off with no occupant) would confirm the second possibility and avert an alarm condition. The cessation of a heart beat needs to be correlated with the presence of a body to cause an alarm, since the absence of body pressure would simply indicate a person leaving the bed. The prevention of false positive type errors is a major advance over other systems, since an alarm could possibly generate a medical alert through an interface software 106 as described below.

3. Interface software 106. At bedtime, the interface software 106 asks the individual questions relating to any activities that happened during the day that might contribute to sleep quality. Some examples are the last time and how much a meal was eaten, consummation of medication, vitamins, and products containing caffeine and alcohol, estimate of stress level, and amount/intensity of exercise. When the person wakes up, a short questionnaire is presented, asking the person to estimate the quality of sleep just experienced. This questionnaire can be administered on a computer with a touch screen, or by voice input, or over the phone, with a small vocabulary of yes, no, and the numbers from 0 to 10 to give information on level or quantity. For example, one question could be phrased as: "On a scale from 1 to 5, rate the quality of your sleep?"

The interface software 106 can also generate alarm messages when the real-time analysis software diagnosed an alarm condition in a person's vital signs.

The user interface software 106 only needs to be activated twice per day at a minimum.

4. Lifestyle correlation software 108. On request by the individual, the computer will be able to deliver a correlation analysis between any of the data inputs, both from the layer pad sensors as well as the interface software 106. Aggregate data on periods from several days to several months can be presented to show long-term averages, trends, and singularities (unusual correlations). The lifestyle correlation software 108 will show the top correlations, in ranked order, to illustrate how lifestyle patterns have an effect on sleep quality. The individual can thereby explore which events, or groups of events, tend to correlate with which others and, based on the data, make lifestyle changes. For example, if a restless night (as evidenced by a high position-change index and bruxism index) correlates well with an absence of exercise for several days, but only in periods characterized with high stress at work, then the correlation analysis would suggest a higher dose of exercise during periods of high work stress to keep the stress from degrading the quality of sleep. These correlations will be highly individual and unpredictable. Long-term data collection, which is not possible in the clinical environment, provides the highest likelihood of statistically and functionally significant outcomes.

5. Active components 110 to improve sleep quality. The system of the present invention can optionally be connected to various active devices to influence the sleep experience. The actuation can be based on data collected from the layer pad, from data accumulated over time, and from established correlations between sleep state and sleep quality, or a combination of these sources. Some examples are a temperature control system that alters the bed or room temperature based on a person's skin temperature or state of restlessness; an alarm can be activated in the morning at a particular point in a person's circadian rhythm; or an active, tilting mattress support can encourage a person to roll over to alleviate a snoring episode. A bed could be designed with a robotic mattress, with individually actuated mattress cells programmed to move in synchrony to move the sleeper. For example, the sensors can monitor pressure points and adjust the person's position or individually adjust mattress cell height to alleviate problems. Also, to help alleviate certain sleep problems like snoring, the mattress could move certain cells up and others down to encourage a person roll over into another position. The mattress could also provide percussion to certain areas of the body, like the chest, to clear up lung problems or physically jolt the heart area externally.

These five components form the key technical elements to the system of the present invention.

Figure 2:
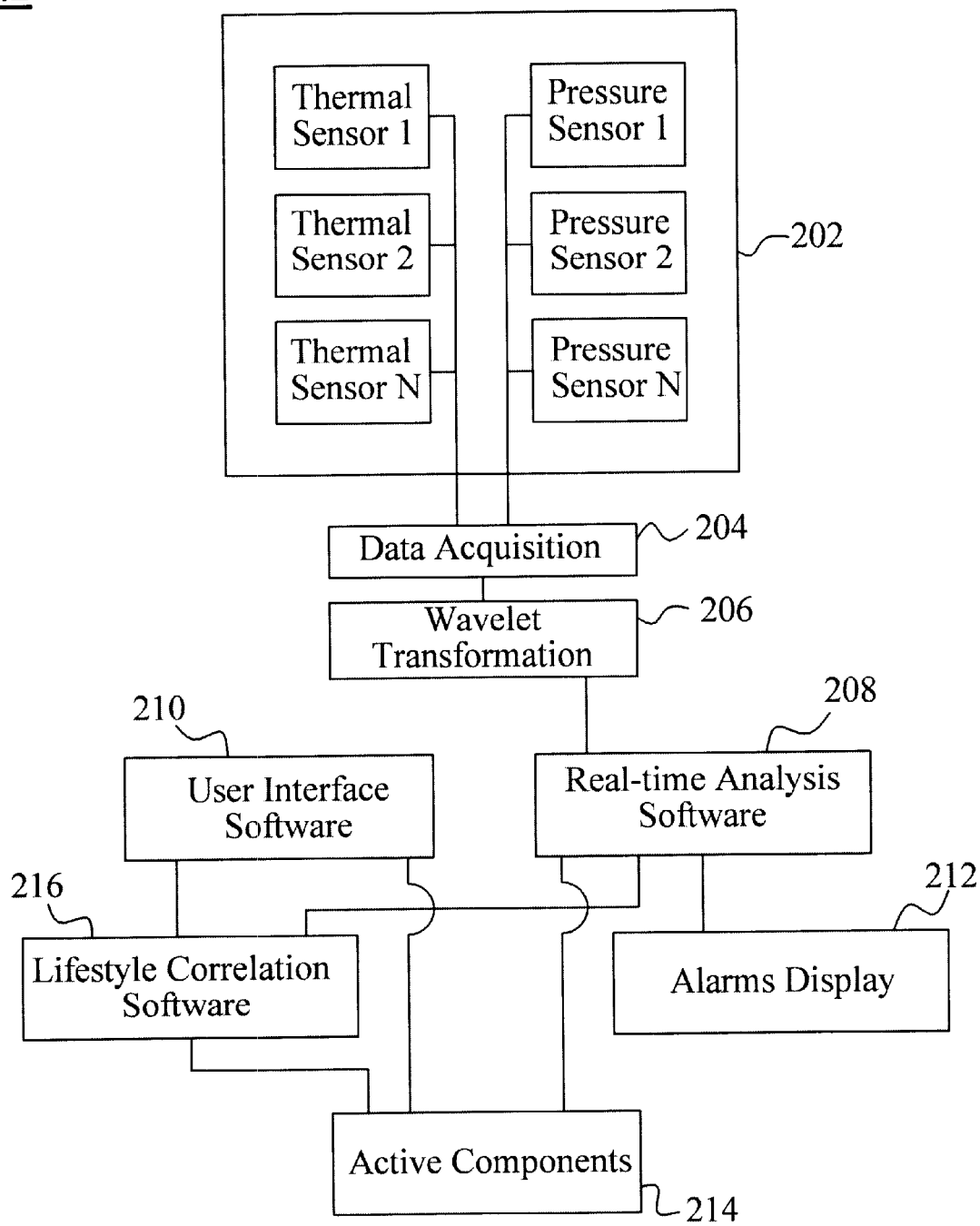
FIG. 2 is a flow diagram illustrating the process of the present invention.

FIG. 2 is a flow diagram illustrating the process of the present invention. Sensor arrays 202 in accordance to the example of FIG. 1 include thermal sensors 1—N and pressure sensors 1—N. The sensor arrays 202 feed data into the data acquisition unit 204 and the data is time based. Using wavelet transformation 206, the data is transformed into event-based, frequency-based, or both. The transformed data is then analyzed in real-time by an analysis software 208. The results from the analysis software 208 can trigger alarms or alarm messages 212. The results can also be used in the lifestyle correlation software 216. The user interface software 210 of the system gathers data from the user such as their perceived quality of sleep just experienced, or whether they ate before a night's sleep. The data from the real-time analysis software 208, the lifestyle correlation software 216, and the user interface software 210 are used to control active components 214 such as dimming lights.

Besides the home-use sleep monitoring application, the system of the present invention also has other significant applications as detailed below.

SIDS application: The layer pads can be made in a small size with higher resolution sensor array to perform home monitoring of babies diagnosed as being at risk for Sudden Infant Death Syndrome (SIDS). An alert can be sounded if the infant stops breathing or the system does not detect a heart beat.

Field vital sign monitoring: The system of the present invention can also be used in emergency situations where vital sign monitoring is necessary, but where instrumentation is lacking or where sterilization is not possible, or where there is no expertise to attach traditional monitoring equipment. The layer pads can be placed under a person on any bed or horizontal surface for instant and hands-free monitoring. In this capacity, it can be used in the field by paramedics in large-scale emergencies.

What is claimed is:

1. An apparatus for monitoring an individual's sleep quality comprising:

one or more layers of arrays of integrated sensors, embedded in a layer pad and said layer pad is laid between a mattress and said individual, wherein said arrays of integrated sensors are distributed with a low spatial resolution and wherein each of said integrated sensors in said layer pad provide different type of data;

one or more controllers coupled with said layers of arrays of integrated sensors for the purpose of acquiring said data from said sensors; and a real-time analysis software for analyzing said data acquired by said controller, wherein said analysis software transforms said data collected by said controller from time domain to event domain using wavelet transformations, frequency domain using wavelet transformations, or event and frequency domain using wavelet transformations.

2. The apparatus as claimed in claim 1 further comprising an interface software for collecting user lifestyle data.

3. The apparatus as claimed in claim 2 wherein said user lifestyle data is one or more data from the group consisting: last time and how much a meal was eaten, how much medication, vitamins, and products containing caffeine and alcohol was consumed, estimate of stress level, amount and intensity of exercise, and an estimation of the quality of sleep just experienced overnight.

4. The apparatus as claimed in claim 2 further comprising a lifestyle correlation software for correlating said lifestyle data with said data.

5. The apparatus as claimed in claim 4 wherein said lifestyle correlation software provides correlation analysis between any of said data collected by said controller and by said interface software.

6. The apparatus as claimed in claim 4 wherein said lifestyle correlation software utilizes aggregate data from several days to several months to compute and present long-term averages, trends, and singularities.

7. The apparatus as claimed in claim 2 further comprising one or more active components to improve sleep quality based on said data acquired through said array of sensors and said lifestyle data.

8. The apparatus as claimed in claim 7 wherein said active components are chosen from a group consisting: a temperature control system to alter said mattress or room temperature based on body temperature data, an alarm activated based on a particular point in a person's circadian rhythm, and an active tilting mattress support activated to encourage a person to roll over to alleviate snoring.

9. The apparatus as claimed in claim 1 further comprising a mattress pad upon which the layer pads are placed.

10. The apparatus as claimed in claim 1 wherein a layer pad of array of sensors provide one or more of the following data: position, temperature, sound, vibration, and movement data.

11. The apparatus as claimed in claim 1 wherein said controller is chosen from a group consisting of: an embedded controller, a desktop personal computer, a laptop computer, and a hand-held portable device.

12. The apparatus as claimed in claim 1 wherein said real-time analysis software can extract means, variances, characteristic frequencies, and counts from said data from said controller and calculate an index of nightly restlessness.

13. The apparatus as claimed in claim 1 wherein said real-time analysis software extracts one or more information in a group consisting of: body temperature, position and movement, mattress pressure, breathing and heart rate, snoring, and bruxism.

14. The apparatus as claimed in claim 1, wherein said one or more layers of said sparse arrays of said integrated sensors are zoned to a specific body area of said individual.

15. A method for monitoring an individual's sleep quality comprising the steps:
   placing one or more layer pads, within which arrays of integrated sensors, wherein said arrays of integrated sensors are distributed with a low spatial resolution and wherein each of said integrated sensors provide different type of data, are embedded, horizontally beneath a subject to be monitored between a mattress and said individual;
   using a controller to acquire said data provided by said arrays of integrated sensors;
   using a real-time analysis software for analyzing said data acquired by said controller from said array of integrated sensors, wherein said analysis software transforms said data collected by said controller from time domain to event domain using wavelet transformations, frequency domain using wavelet transformations, or event and frequency domain using wavelet transformations.

16. The method as claimed in claim 15 further comprising using an interface software for collecting user lifestyle data.

17. The method as claimed in claim 16 wherein said user lifestyle data is one or more data from the group consisting: last time and how much a meal was eaten, how much medication, vitamins, and products containing caffeine and alcohol was consumed, estimate of stress level, amount and intensity of exercise, and an estimation of the quality of sleep just experienced overnight.

18. The method as claimed in claim 16 further comprising using a lifestyle correlation software for correlating said lifestyle data with said data acquired by said array of sensors.

19. The method as claimed in claim 18 wherein said lifestyle correlation software provides correlation analysis between any of said data collected by said controller and by said interface software.

20. The method as claimed in claim 18 wherein said lifestyle correlation software utilizes aggregate data from several days to several months to compute and present long-term averages, trends, and singularities.

21. The method as claimed in claim 16 further comprising using one or more active components to improve sleep quality based on said data acquired through said array of sensors and said lifestyle data.

22. The apparatus as claimed in claim 21 wherein said active components are chosen from a group consisting: a temperature control system to alter said mattress or room temperature based on body temperature data, an alarm activated based on a particular point in a person's circadian rhythm, and an active tilting mattress support activated to encourage a person to roll over to alleviate snoring.

23. The method as claimed in claim 15 further comprising a mattress pad upon which the layer pads are placed.

24. The method as claimed in claim 15 wherein a layer pad of array of sensors provide one or more of the following data: position, temperature, sound, vibration, and movement data.

25. The method as claimed in claim 15 wherein said controller is chosen from a group comprising: an embedded controller, a desktop personal computer, laptop computer, and a hand-held portable device.

26. The method as claimed in claim 15 wherein said real-time analysis software extracts one or more information in a group consisting of: body temperature, position and movement, mattress pressure, breathing and heart rate, snoring, and bruxism.

27. The method as claimed in claim 15 wherein said real-time analysis software can extract means, variances, characteristic frequencies, and counts from said data from said controller and calculate an index of nightly restlessness.

28. The method as claimed in claim 15, wherein said one or more layers of said sparse arrays of said integrated sensors are zoned to a specific body area of said subject.

* * * * *